US00PP12636P2

(12) United States Plant Patent
Fruehwirth

(10) Patent No.: US PP12,636 P2
(45) Date of Patent: May 21, 2002

(54) POINSETTIA PLANT NAMED 'ECKADDIE'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/432,711

(22) Filed: Nov. 2, 1999

(51) Int. Cl.[7] ..... A01H 5/00
(52) U.S. Cl. ..... Plt./303

(58) Field of Search ..... Plt./303

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Eckaddie', characterized by its red and pink-flecked bracts; response time about 10 weeks; very dark green leaves; compact, dense and upright plant habit; rounded canopy; very freely branching habit; and excellent postproduction longevity.

2 Drawing Sheets

BACKGROUND OF THE INVENTION

The present invention relates to a new and distinct cultivar of Poinsettia plant, botanically known as *Eurphorbia pulcherrima* Willd., and hereinafter referred to by the name 'Eckaddie'.

The new Poinsettia is a product of a mutation induction breeding program conducted by the Inventor in Encinitas, Calif. The objective of the Inventor's Poinsettia development program is to create new Poinsettia cultivars having interesting bract and leaf display, desirable bract and foliage color and form, strong and freely branching stems and good post-production longevity.

The new Poinsettia originated by exposing unrooted cuttings of the *Euphorbia pulcherrima* Willd. cultivar Red Splendor, disclosed in U.S. Plant Pat. No. 9,632, to gamma-ray radiation at a level of 3,000 rads. The new Poinsettia was discovered and selected by the Inventor in December, 1997. The selection of this plant was based on its unique bright red and pink-flecked bract color.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckaddie'. These characteristics in combination distinguish 'Eckaddie' as a new and distinct cultivar:

1. Bright red bracts with random pink flecks.
2. Response time about 10 weeks.
3. Very dark green leaves which provide an excellent contrast to the bright red and pink-flecked bracts.
4. Compact, dense and upright plant habit; rounded canopy.
5. Very freely branching habit.
6. Excellent postproduction longevity.

In side-by-side comparisons conducted in Encinitas, Calif., plants of the new Poinsettia and the parent cultivar Red Splendor differ primarily in bract coloration as Red Splendor has solid bright red-colored bracts. In addition, plants of the new Poinsettia are more compact and flower about 4 or 5 days later than plants of 'Red Splendor'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckaddie'.

The photograph at the bottom top of the first sheet comprises a top perspective view of a typical plant of 'Eckaddie'.

The photograph on the second sheet is a close-up view of typical bracts and leaves of 'Eckaddie' (left) and 'Red Splendor' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures ranging from 21 to 27° C., night temperatures ranging from 18 to 20° C., and light levels about 4,000 foot-candles. Plants were grown in 16-cm pots, pinched one time, and flowered under naturally lengthening nyctoperiods during the fall/early winter.

In the following description, color references are made to The Royal Horticultural Society Colour Chart except where general terms of ordinary dictionary significance are used.

Botanical classification: *Euphorbia pulcherrima* Willd. 'Eckaddie'.

Parentage: Induced mutation of *Eurphorbia pulcherrima* Willd. cultivar Red Splendor, disclosed in U.S. Plant Pat. No. 9,632.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Rooting habit.*—Freely branching, becoming fibrous with development.

Plant description:

*Plant form.*—Inverted triangle; rounded canopy.

*Growth habit.*—Compact and dense; upright. Very freely branching. Branching is enhanced by removing the shoot apex. Moderately vigorous.

*Plant height.*—About 25 cm.

*Crop time.*—From unrooted cuttings to a flowering plant in a 16-cm container, about 18 weeks are required.

*Stem description.*—Number of lateral branches: About nine lateral branches are formed after removal of the terminal apex. Lateral branch length: About 18 cm. Internode length: About 7.5 mm. Stem color: 146A.

*Foliage description.*—Quantity of leaves per lateral branch: About 10. Length: About 9 cm. Width: About 6.25 cm. Shape: Mostly ovate with irregular rounded lobes. Apex: Acuminate. Base: Acute. Margin: Entire. Texture: Smooth, velvety; very sparse pubescence on lower surface. Color: Young foliage, upper surface: 147A. Young foliage, lower surface: 146A. Mature foliage, upper surface: Almost black, much darker than 139A, close to 202A. Mature foliage, lower surface: 139A. Venation, upper surface: 145A. Venation, lower surface: 147C. Petiole: Length: About 3.75 cm. Diameter: About 2 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Late flowering, response time is about 10 weeks.

*Quantity of inflorescences.*—One per lateral branch, usually about nine per plant.

*Inflorescence size.*—Diameter: About 22.5 cm. Height (depth): About 4 cm.

*Flower bracts.*—Quantity of flower bracts per inflorescence: Usually about 12 primary bracts and about 6 smaller secondary bracts per inflorescence. Length, largest bracts: About 12 cm. Width, largest bracts: About 8 cm. Shape: Mostly ovate with irregular rounded lobes. Apex: Acuminate. Base: Acute. Margin: Entire. Texture: Smooth, velvety; concave. Aspect: Mostly horizontal. Color: Bright red with random pink flecks. Developing, upper surface: Background, darker than 45A; flecks, 47D. Developing, lower surface: Background, more rose than 45B; flecks, 48C. Mature, upper surface: Background, brighter cherry-scarlet than 45A; flecks, 48C. Mature, lower surface: Background, 45B; flecks, 48C.

*Cyathia.*—Quantity: Usually about 15 per corymb. Diameter of cyathia cluster: About 2 by 2.5 cm. Length: About 1 cm. Width: About 6 mm. Color: Immature: 144A. Mature: 144A to 144B. Peducle: Length: About 2 mm. Aspect: Strong, erect. Color: 144B. Stamens: Stamen number: Numerous, more than 20 with numerous stamenoids per cyathium. Anther length: About 1 mm. Anther shape: Oval. Anther color: 45A. Amount of pollen: Moderate. Pollen color: 14A. Pistils: No pistillate flowers observed. Nectary color: 14A to 14B.

Disease resistance: Plants of the new Poinsettia have been observed to be resistant to Botrytis.

Postproduction longevity: Excellent; generally plants maintain good substance and bract color for about eight weeks under interior conditions.

It is claimed:

1. A new and distinct cultivar of Poinsettia plant named 'Eckaddie', as illustrated and described.

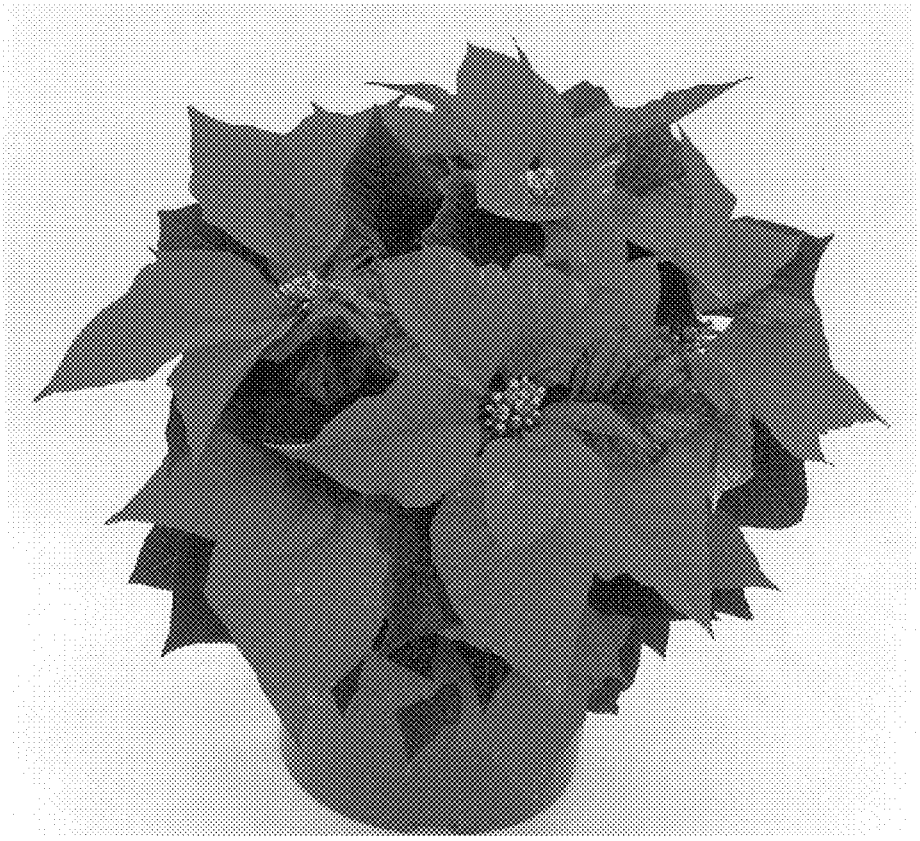
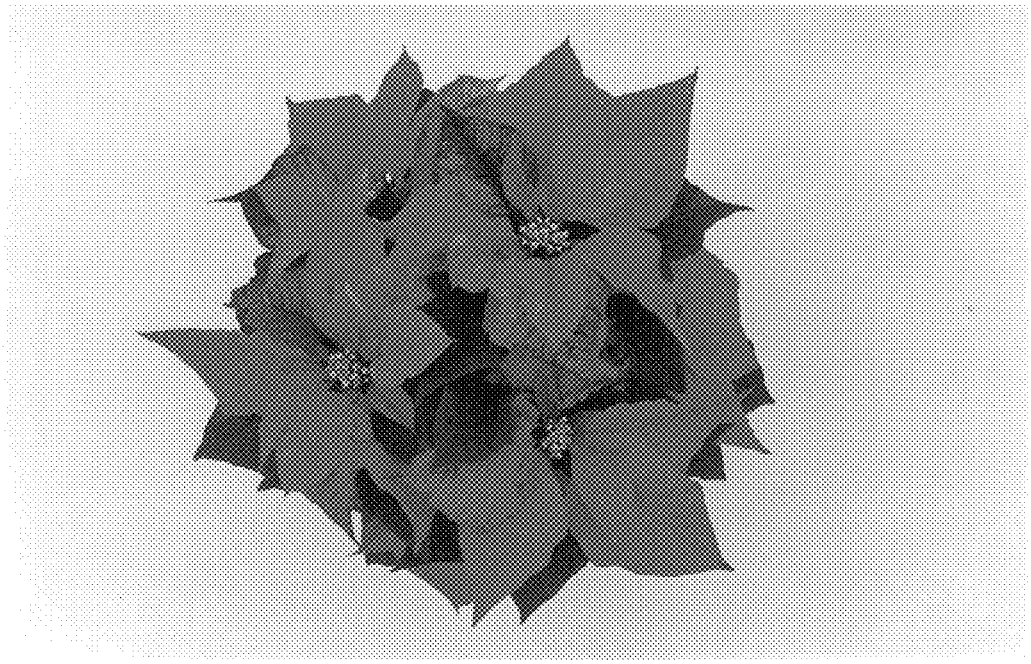

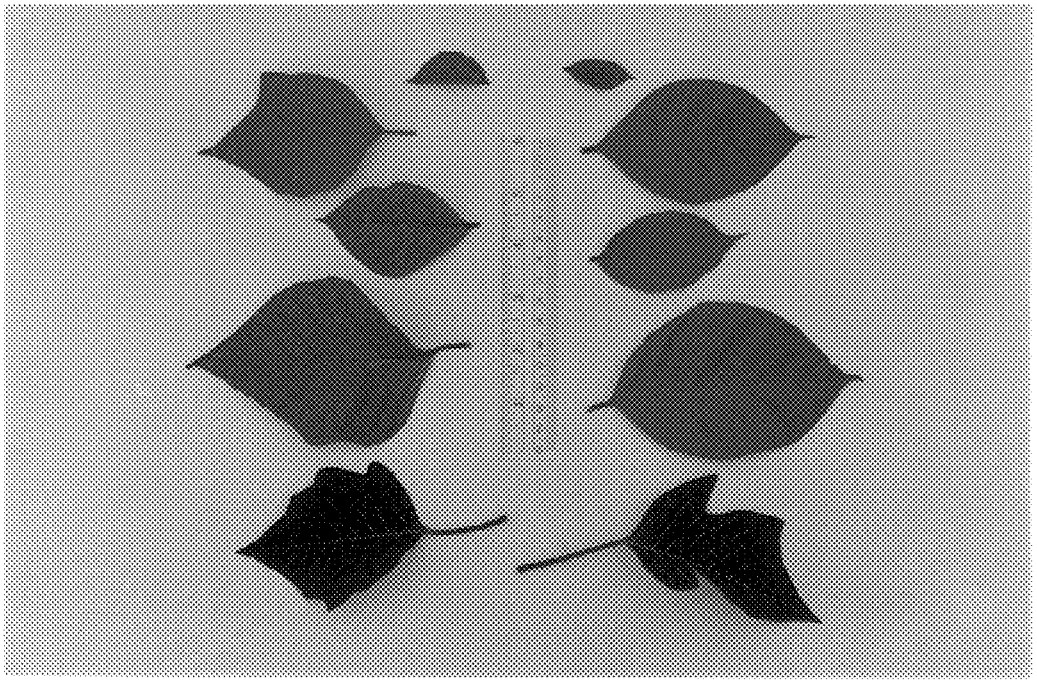

* * * * *